(12) United States Patent
Ding (10) Patent No.: US 8,307,697 B2
(45) Date of Patent: Nov. 13, 2012

(54) METHOD FOR ESTIMATING VISCOSITY

(75) Inventor: Zhong Ding, Pittsford, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 304 days.

(21) Appl. No.: 12/759,809

(22) Filed: Apr. 14, 2010

(65) Prior Publication Data

US 2011/0252872 A1    Oct. 20, 2011

(51) Int. Cl.
*G01N 11/00* (2006.01)
(52) U.S. Cl. ............. 73/54.01; 73/54.04; 73/54.09; 73/54.14
(58) Field of Classification Search .......... 73/54.14, 73/54.01, 54.04, 54.09
See application file for complete search history.

(56) References Cited

U.S. PATENT DOCUMENTS

| | | | |
|---|---|---|---|
| 4,496,293 A | 1/1985 | Nakamura et al. | |
| 4,743,561 A | 5/1988 | Shaffar | |
| 5,452,619 A * | 9/1995 | Kawanabe et al. | 73/864.01 |
| 5,488,874 A * | 2/1996 | Kawanabe et al. | 73/863.01 |
| 5,540,081 A | 7/1996 | Takeda et al. | |
| 5,750,881 A | 5/1998 | Dorenkott et al. | |
| 5,885,530 A | 3/1999 | Babson et al. | |
| 6,060,320 A | 5/2000 | Dorenkott et al. | |
| 6,484,556 B1 | 11/2002 | Jabobs et al. | |
| 6,797,518 B1 | 9/2004 | Jacobs et al. | |
| 7,250,303 B2 | 7/2007 | Jakubowicz et al. | |
| 7,312,084 B2 | 12/2007 | Jakubowicz et al. | |
| 7,402,282 B2 | 7/2008 | LaCourt et al. | |
| 7,926,325 B2 * | 4/2011 | Kaplit | 73/37 |
| 2003/0022380 A1 | 1/2003 | Jakubowicz et al. | |
| 2003/0158500 A1 * | 8/2003 | Kensey et al. | 600/573 |
| 2011/0121016 A1 * | 5/2011 | De Grood et al. | 222/1 |

* cited by examiner

*Primary Examiner* — Hezron E Williams
*Assistant Examiner* — Hoang Nguyen
(74) *Attorney, Agent, or Firm* — Todd J. Burns (57) ABSTRACT

A method for estimating the viscosity of a liquid in an aspirating or dispensing probe, includes: measuring a reference pressure which is the pressure inside a metering tip when no dispense or aspirate is occurring ($P_{ref}$); dispensing or aspirating a liquid having a volume of air between the liquid and the pumping mechanism of the probe; stopping the aspirate or dispense; measuring the pressure ($P_{stop}$) inside the tip at a time (t) which is the time when the aspirate or dispense is stopped; measuring the pressure ($P_{stop'}$) inside the tip at a time (t') after t; and estimating viscosity as a function of $P_{ref}$, $P_{stop}$, and $P_{stop'}$. In a preferred embodiment, the method is carried out on a diagnostic analyzer.

20 Claims, 12 Drawing Sheets

METHOD FOR ESTIMATING VISCOSITY

BACKGROUND OF THE INVENTION

The present invention relates to estimating the viscosity of a liquid in a metering system, such as a liquid transported by a metering system on a diagnostic analyzer. In particular, the present invention relates to estimating viscosity by selected pressure measurements to more accurately determine an amount of fluid aspirated or dispensed.

Figure 1:
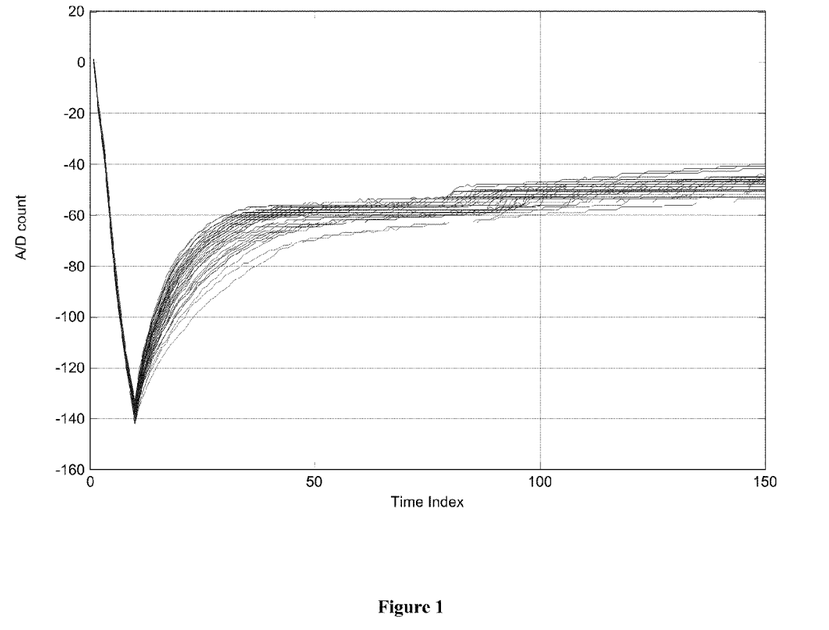
FIG. 1 shows a pressure profile for a 2 μL microtip blood sample aspiration with pressure being shown as A/D counts.

In the diagnostic field, there is a trend for using smaller and smaller amounts of liquid in a diagnostic analysis or assay, such as on a diagnostic analyzer. Thus precise and accurate handling of small, e.g., micro liters, volumes of fluid is important to the performance of an assay being performed. The performance of available liquid metering systems, such as those on diagnostic analyzers, is sensitive to liquid properties, such as viscosity, in part because a higher viscosity liquid is more likely to adhere to the surface of an aspirating probe or the metering tip of such a probe, and also leads to the aspiration of less liquid than intended. The pressure signature or profile of the gas, e.g., air, between the pumping mechanism and the liquid during metering is a function of liquid viscosity. A typical pressure profile is shown in FIG. 1.

Known viscosity estimation techniques for metering systems, in known diagnostic analyzers generally work only for aspiration volumes larger than 35 μL. Such metering systems can be used on known diagnostic analyzers such as the Vitros 5600 and Vitros 3600 diagnostic analyzer sold by Ortho-Clinical Diagnostics, Inc. and other known analyzer systems because such analyzer typically measure volumes of liquid that are greater than 35 μL.

Thus, there is a need for a satisfactory estimation of liquid viscosity when small volumes of liquids, e.g., less than 35 μL and much less, are involved in a metering process, such as aspirating or dispensing a liquid.

SUMMARY OF THE INVENTION

The present invention is directed to a method that solves the foregoing problems of being able to estimate viscosity at relatively small liquid volumes, particularly in the context of metering liquids during a metering operation on a diagnostic analyzer.

One aspect of the invention is directed to a method for estimating the viscosity of a liquid in an aspirating or dispensing probe. The method includes: measuring a reference pressure which is the pressure inside a metering tip when no dispense or aspirate is occurring ($P_{ref}$); dispensing or aspirating a liquid having a volume of air between the liquid and the pumping mechanism of the probe; stopping the aspirate or dispense; measuring the pressure ($P_{stop}$) inside the tip at a time (t) which is the time when the aspirate or dispense is stopped; measuring the pressure ($P_{stop'}$) inside the tip at a time (t') after t; and estimating viscosity as a function of $P_{ref}$, $P_{stop}$, and $P_{stop'}$.

In one embodiment, the method above further includes: calculating a relative pressure difference ($\bar{p}$) which is the difference between $P_{stop}$ and $P_{ref}$; calculating the rate of pressure change ($\dot{\bar{p}}$) at $P_{stop}$ by $\dot{\bar{p}} = (P_{stop'} - P_{stop})/(t'-t)$; and estimating viscosity as a function of $\bar{p}$ and $\dot{\bar{p}}$.

In another embodiment, the method above further includes: calculating a rate of pressure rise $$(R) = \frac{P_{stop+3} - P_{stop}}{P_{stop} - P_{ref}};$$

and estimating viscosity as a function of R.

Another aspect of the invention provides, a method for aspirating a selected amount of liquid. The method includes: providing an aspirating probe which comprises a probe tip and a pump, wherein the probe tip and pump are in fluid communication; measuring a reference pressure which is the pressure inside a metering tip when no dispense or aspirate is occurring ($P_{ref}$); moving the tip into the liquid, whereby a volume of gas is located between the top of the liquid and the pump, wherein the reference pressure is measured before or after the tip enters the liquid; actuating the pump for a duration or distance which corresponds to a selected volume of liquid to be aspirated; stopping the aspirate or dispense; measuring the pressure ($P_{stop}$) inside the tip at a time (t) which is the time when the aspirate or dispense is stopped; measuring the pressure ($P_{stop'}$) inside the tip at a time (t') after t; estimating viscosity as a function of $P_{ref}$, $P_{stop}$, and $P_{stop'}$; compensating for viscosity by either notifying an operator if the estimated viscosity is outside a predetermined range, or adjusting the actuation of the pump based on the estimated viscosity. In one embodiment, the pump is a piston pump and wherein the piston of the piston pump is moved a predetermined distance which corresponds to a selected volume of liquid to be aspirated.

Yet another aspect of the invention provides a method of analyzing a sample for an analyte. The method includes: providing a source of a sample;

providing an aspirating probe which comprises a probe tip and a pump, wherein the probe tip and pump are in fluid communication; measuring a reference pressure which is the pressure inside a metering tip when no dispense or aspirate is occurring ($P_{ref}$); moving the tip into the liquid, whereby a volume of gas is located between the top of the liquid and the pump, wherein the reference pressure is measured before or after the tip enters the liquid; actuating the pump for a duration or distance which corresponds to a selected volume of liquid to be aspirated; stopping the aspirate or dispense; measuring the pressure ($P_{stop}$) inside the tip at a time (t) which is the time when the aspirate or dispense is stopped; measuring the pressure ($P_{stop'}$) inside the tip at a time (t') after t; estimating viscosity as a function of $P_{ref}$, $P_{stop}$, and $P_{stop'}$; compensating for viscosity by either notifying an operator if the estimated viscosity is outside a pre-determined range, or adjusting the actuation of the pump based on the estimated viscosity.

Further objects, features and advantages of the present invention will be apparent to those skilled in the art from detailed consideration of the preferred embodiments that follow.

DETAILED DESCRIPTION OF PREFERRED EMBODIMENTS

While the various applications for estimating viscosity according to the invention is not limited, a particularly useful application is in the field of diagnostic analysis. The range of analyzers and methodologies that can be used with the present invention is large and is discussed in more detail below.

As used herein, a "small volume" or "relatively small volume" of liquid is defined as generally $\leq 35$ µL, $\leq 25$ µL, $\leq 20$ µL, $\leq 10$ µL, $\leq 5$ µL and even less than 2 µL and particularly volumes $\leq 20$ µL.

In the following description of the preferred embodiments of the invention, a piston pump is described, however, other pumping mechanisms such as a diaphragm pump can be used with the present invention.

An aspect of the present invention uses select pressure measurements during a metering event to estimate liquid viscosity when the aspirated liquid volume is a small volume. While not wishing to be bound by any theory, the present invention is premised on the inventors' discovery that viscosity estimation be determined based on the measurement of pressure only. The inventor, through the following derivation(s), was able to demonstrate that viscosity could be estimated based on pressure measurements at selected times of the metering event only.

This is accomplished by measuring the relative pressure (defined below) and estimating the fluid flow rate (Q) by measuring the rate of pressure change at pump stop (defined below). The relative pressure (DP or) and the fluid flow rate (Q) are then used to correlate to liquid viscosity.

During liquid aspiration, the piston of a piston pump withdraws, and the pressure inside the tip decreases due to viscosity and inertia of the aspirated liquid (FIG. 1). At the time when piston stops, a lower pressure is created inside the tip. The pressure difference or relative pressure DP between the ambient pressure and the pressure inside of the tip continues to drive liquid flowing into the tip after the pump stops until the pressure reaches equilibrium.

The pressure when the pump is stopped (pump stop) is related to the viscosity of the liquid pumped. The higher the viscosity, the lower the pressure, when other all conditions remain the same. The flow rate (Q) of liquid at pump stop is proportional to the pressure difference (DP) between the inside of the tip and ambient (i.e., outside the tip) and is inversely proportional to liquid viscosity. It should be noted that this relationship applies at all times, not only at pump stop and the liquid inertia is negligible due to the small liquid mass involved.

At pump stop, the liquid flow rate (Q) is the same as the rate of air volume change of air inside the tip. The rate of air volume change can be determined by measuring the air pressure change inside the tip. In one embodiment, the air pressure is measured by the A/D (analog to digital) count from the pressure sensor in the metering system. The rate of measured pressure A/D count is proportional to the difference between the piston rate and liquid flow rate. If pump stops, the rate of measured pressure change is proportional to liquid flow rate.

The relative pressure (DP) at pump stop between the inside and the outside of the tip (ambient) can be calculated by $DP = P_{stop} - P_{ref}$, where $P_{stop}$ is the pressure when the pump stops and $P_{ref}$ is the ambient pressure before aspiration. The liquid flow rate (Q) after pump stop is proportional to the pressure difference between the inside and outside of the tip. As described above, the flow rate (Q) is also inversely proportional to liquid viscosity. Therefore the liquid viscosity can be estimated with a function $\mu = f(Q, DP)$.

As described above, after pump stop the liquid flow rate in the tip is proportional to the rate of air pressure change, $Q = \alpha(P_2 - P_1)/(t_2 - t_1)$, where $P_1$ is the pressure at time $t_1$ and $P_2$ is the pressure at $t_2$ and $\alpha$ is a constant.

In a preferred embodiment, the pressures at the time when the pump stops and 3 time indexes later (described more fully below) are selected to calculate the flow rate with $Q = \beta(P_{stop+3} - P_{stop})$, where $\beta$ is a constant. Liquid viscosity is estimated by $$\mu = f(\tilde{R})$$

$$\text{Where } R = \frac{P_{stop+3} - P_{stop}}{P_{stop} - P_{ref}}.$$

In this derivation, viscosity is a function of parameter R. R is called the rate of pressure rise and is calculated by the three pressure points ($P_{stop+3}$, $P_{stop}$, $P_{ref}$) in the pressure signature during aspiration. The function $f$ is a selected calibration model that generates a best fit for the relationship between parameter R and viscosity $\mu$.

FIG. 1 shows pressure signature when aspirating 2 µL blood having similar but different viscosities graphed as pressure as a function of time. The higher the curve relative to A/D count, the lower the viscosity. The valley in FIG. 1 corresponds to pump stops ($P_{stop}$). Pressure rises slower for higher viscosity liquid as particularly shown by the three (3) lowest curves.

Figure 2:
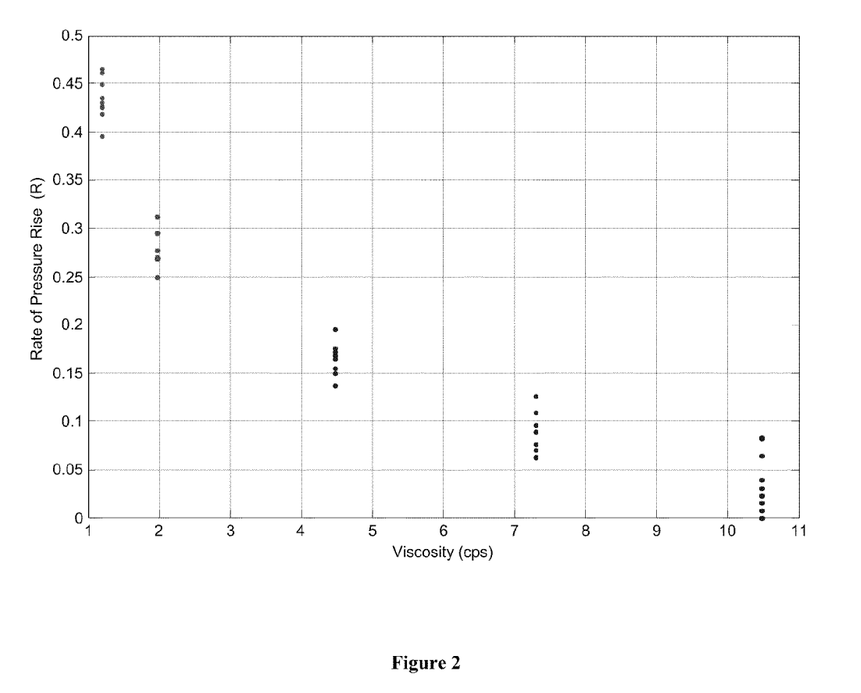
FIG. 2 shows a graph of rate of pressure rise (R) as a function of viscosity for liquids having differing viscosities.

FIG. 2 shows rate of pressure rise R (as determined by three pressure measurements) as function of viscosity $\mu$ for serum samples having a range of viscosities.

Curve fitting can be carried out using known models such as log it/log 4. Other known calibration models can also be used such as the curve fitting model described below.

Figure 3:
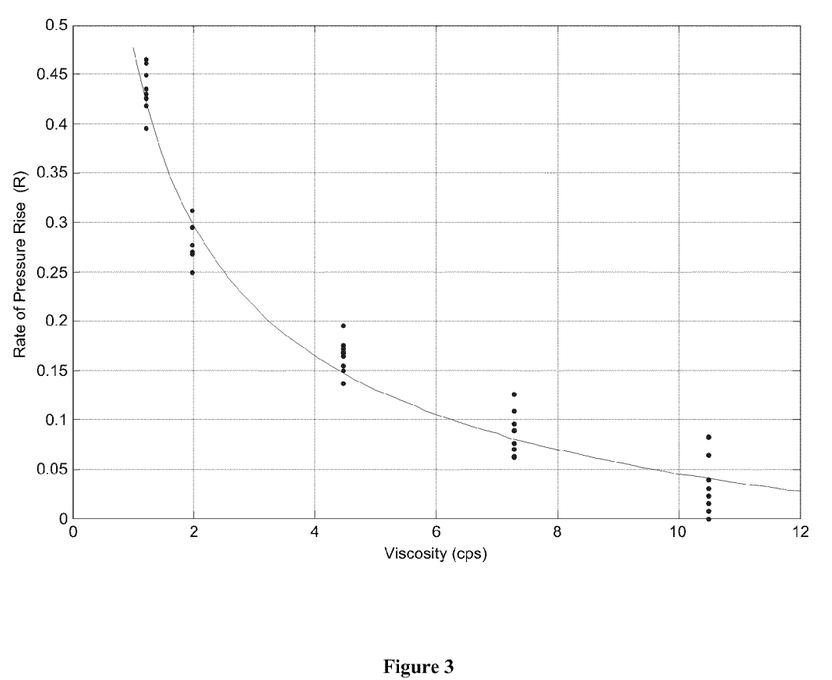
FIG. 3 shows a curve of rate of pressure rise as a function of viscosity using the log it/log 4 curve fitting model for liquids having differing viscosities.

Log it/log 4 is used as calibration model to correlate viscosity with rate of pressure rise R. FIG. 3 shows the Log it/Log 4 calibration curve with $$\mu = \beta_0 + \frac{\beta_1}{1 + e^{-(\beta_2 + \beta_3 \ln R)}}.$$

The viscosity is predicted by $$\mu = e^{\left\{-\frac{1}{\beta_3}\left[\beta_2 + \ln\left(\frac{\beta_1}{R-\beta_0}-1\right)\right]\right\}}.$$

The four constants $\beta_0$, $\beta_1$, $\beta_2$, and $\beta_3$ for the serum samples of FIG. 3 are $\beta_0 = -0.1709$, $\beta_1 = 19.2872$, $\beta_2 = -3.3593$, and $\beta_3 = -0.4868$. The constants $\beta_0$, $\beta_1$, $\beta_2$, and $\beta_3$ are determined by known rate of pressure rise R and known viscosities. Thus, when R=0.2, the estimated or predicted viscosity is 3.243 cps.

Another curve fitting model is $$\mu = B0 + \frac{B1}{R+B2}.$$

Figure 4:
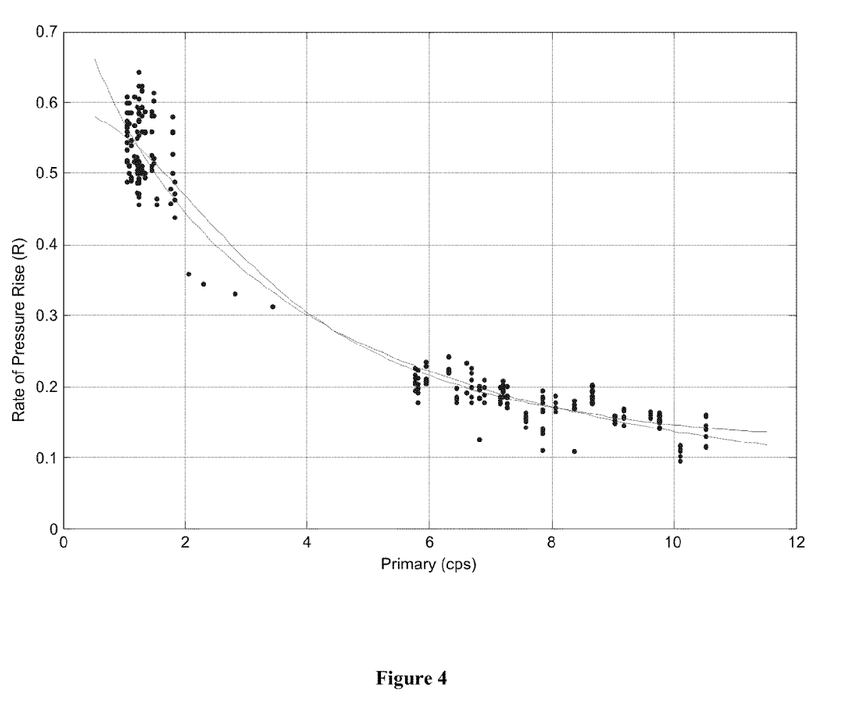
FIG. 4 shows two curves of rate of pressure rise as a function of viscosity using the log it/log 4 curve fitting model (solid line) and another curve fitting technique (dashed line).

For data collected from whole blood as shown in FIG. 4, the model fitted is shown as a dashed curve with B0=−0.0508, B1=−2.4206, B2=−2.8811. The solid curve was plotted using the log it/log 4 model described above.

Figure 5:
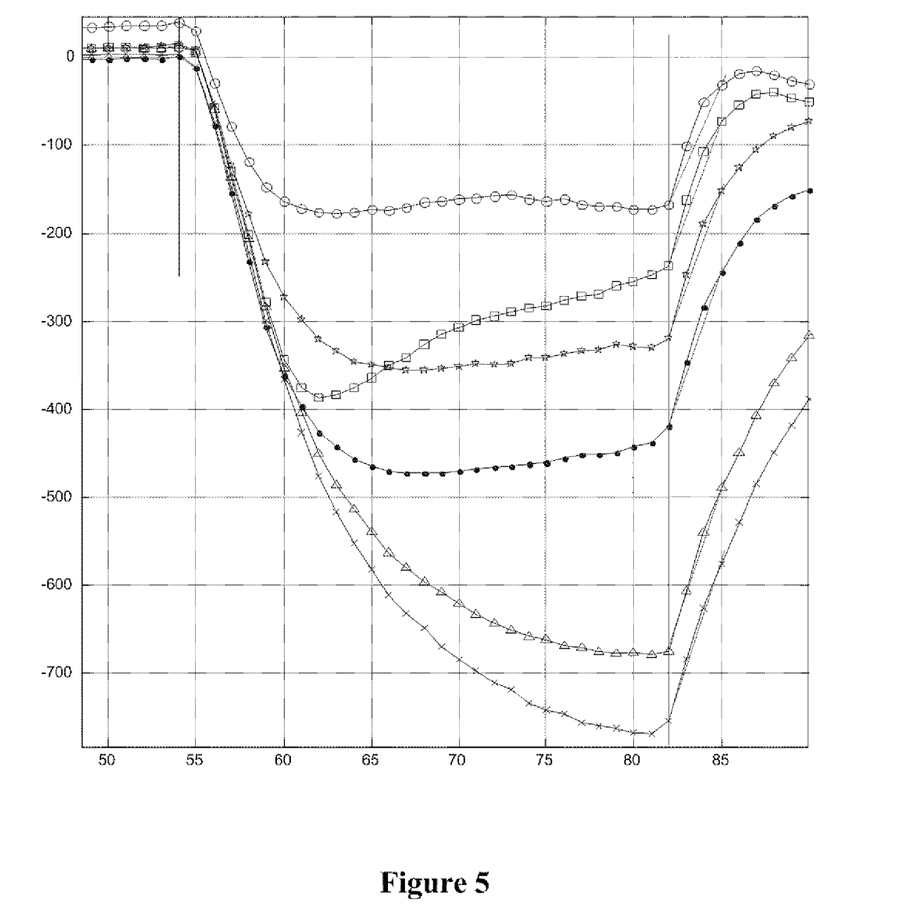
FIG. 5 shows pressure profiles during the aspiration of liquids as a function of time for a 7.5 µL aspiration with different viscosities.

FIG. 5 depicts a pressure trace as function of time index for a 7.5 μL aspiration with different viscosities.

Figure 6A:
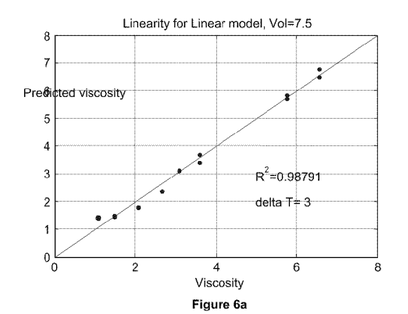
FIGS. 6a-d show the linearity and error for the linear calibration model (up) and log it/log 4 calibration model.
Figure 6B:
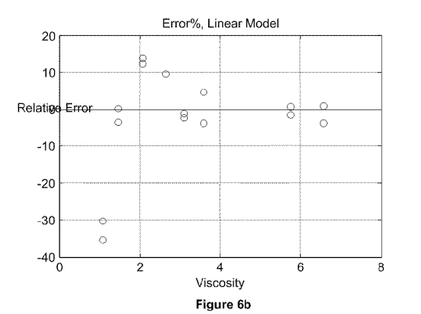
Figure 6C:
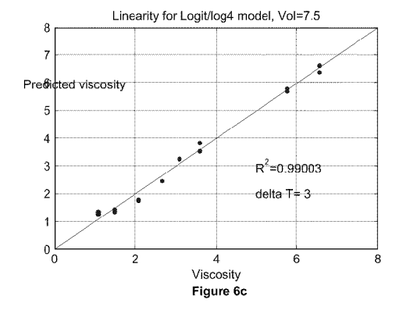
Figure 6D:
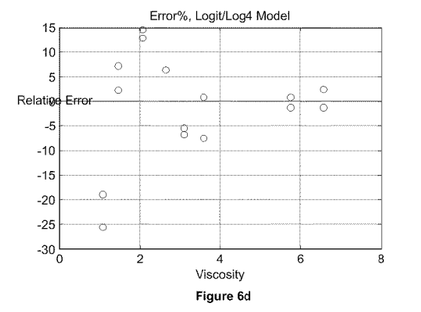

FIGS. 6*a*-*d* depict the linearity for linear calibration model (up) and the model log it/log 4 calibration model. FIGS. 6*b* and 6*d* show that as the viscosity increases the relative error decreases.

Figure 7:
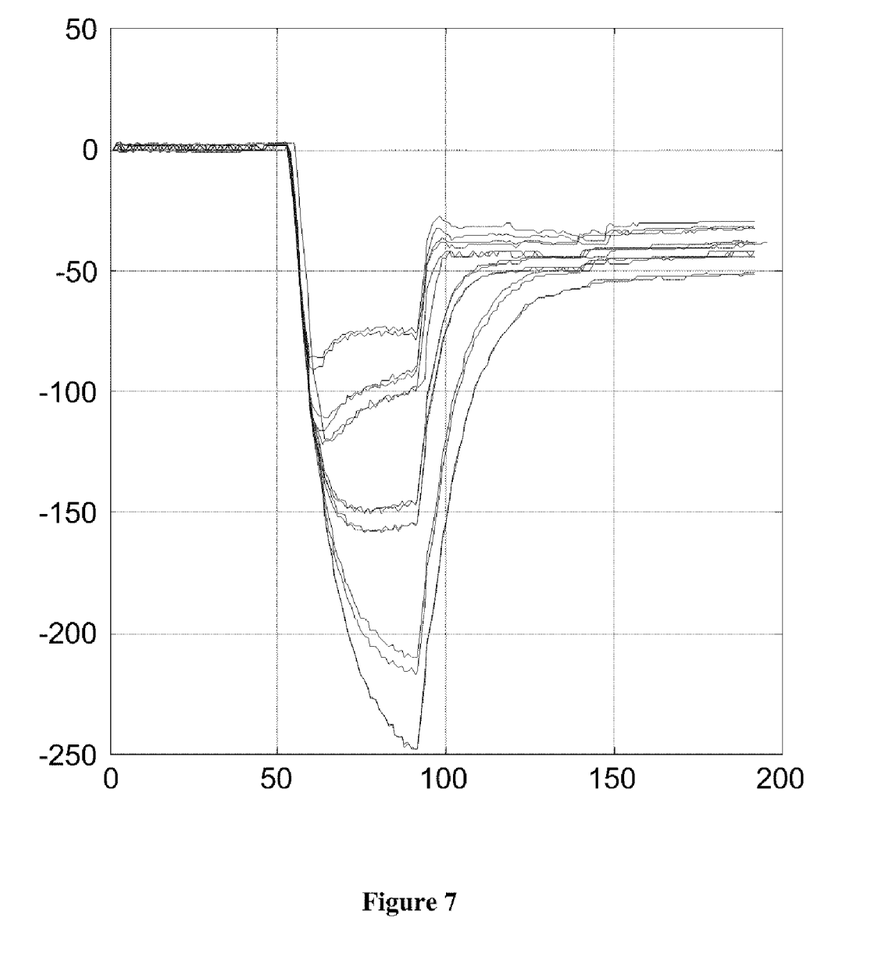
FIG. 7 shows pressure profiles during an aspiration of liquids as a function of time for an 11 µL aspiration with different viscosities.

FIG. 7 shows pressure profiles for different viscosity fluids whose viscosity was determined by a rotational viscometer.

Figure 8:
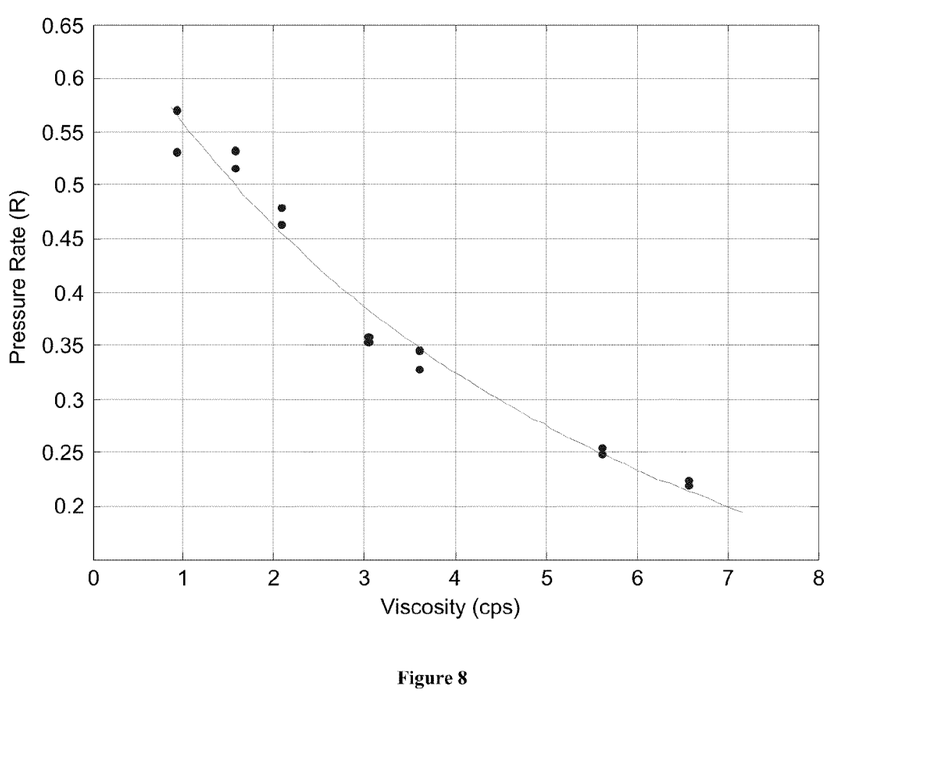
FIG. 8 shows pressure rate as a function of viscosity for an 11 µL liquid sample aspiration with liquids having different viscosities.
Figure 9:
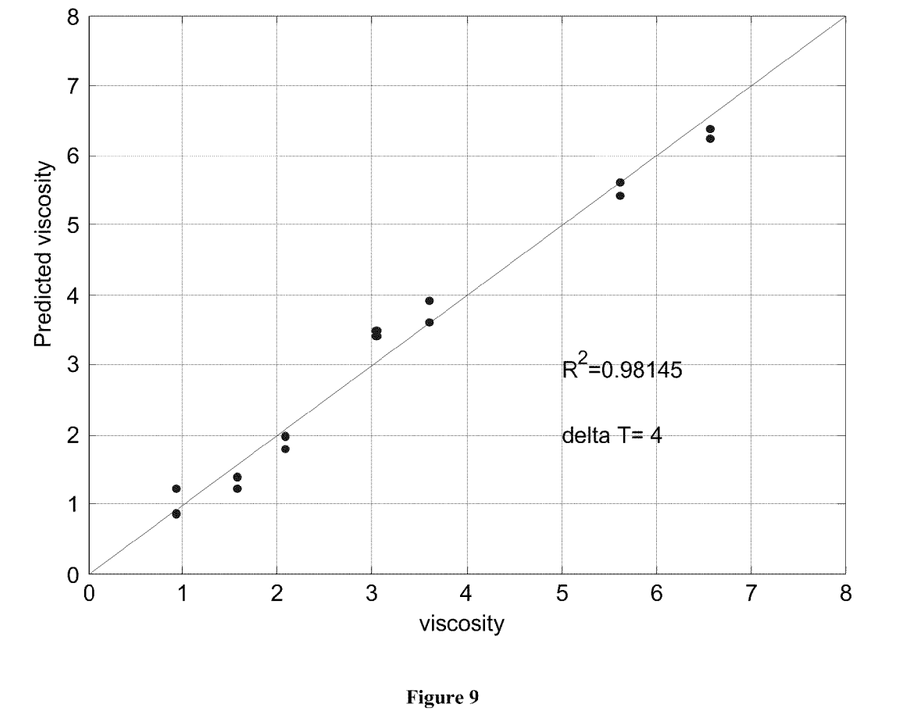
FIG. 9-15 are graphs showing the linearity of predicted viscosity vs. true or actual viscosity using the log it/log 4 model for various viscosities.
Figure 10:
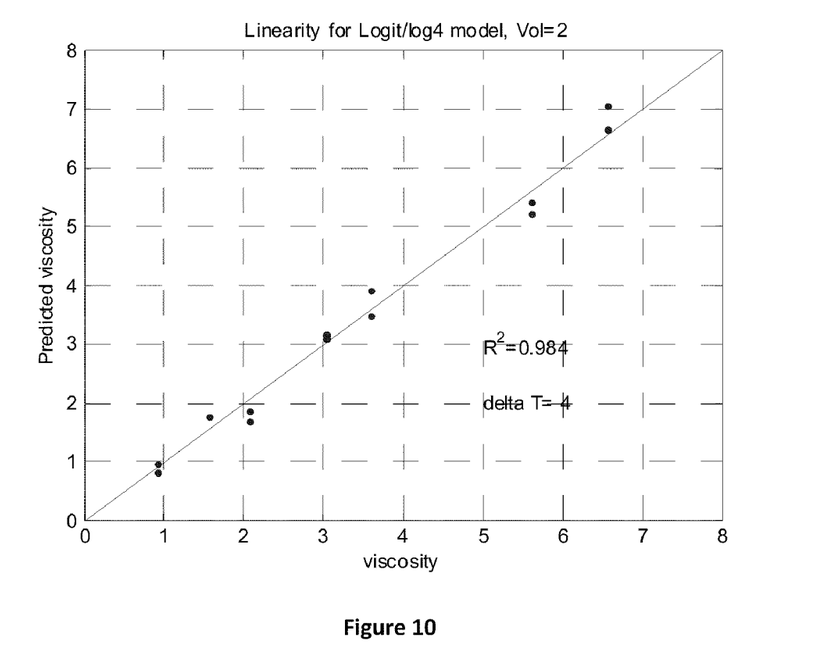
Figure 11:
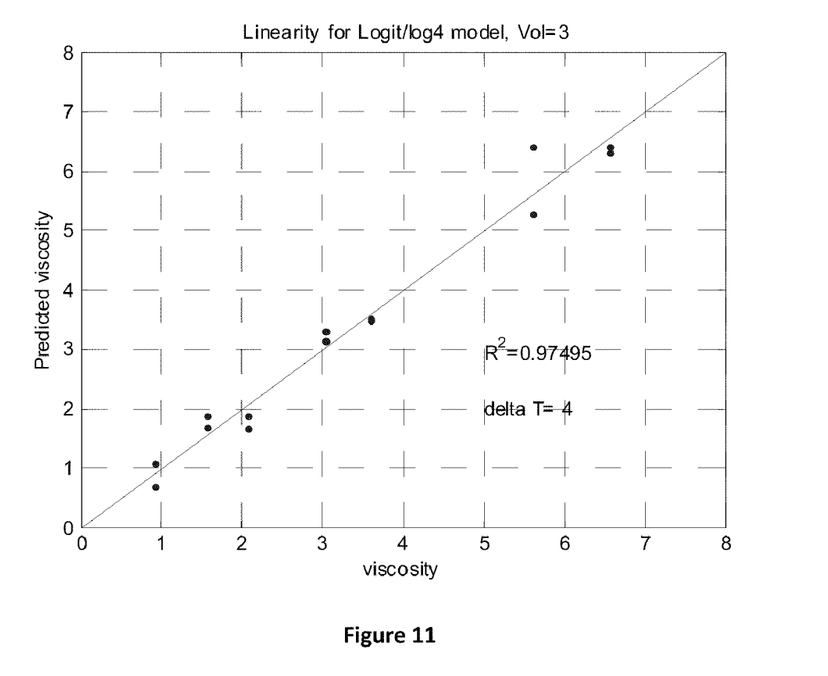
Figure 12:
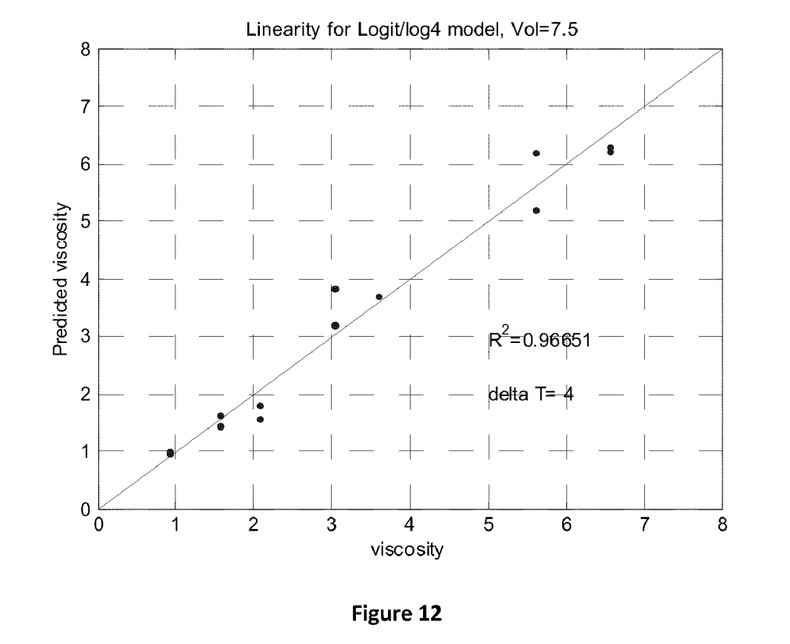
Figure 13:
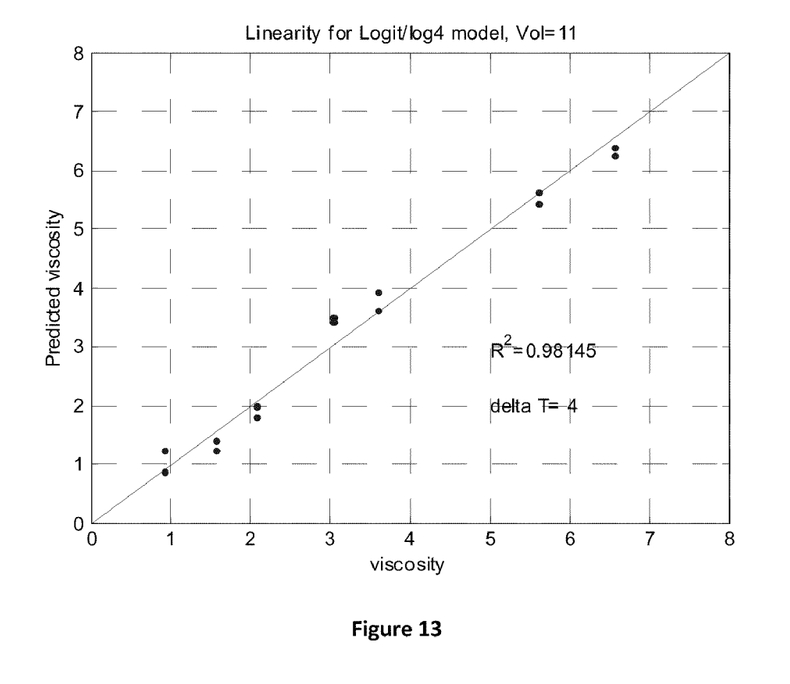
Figure 14:
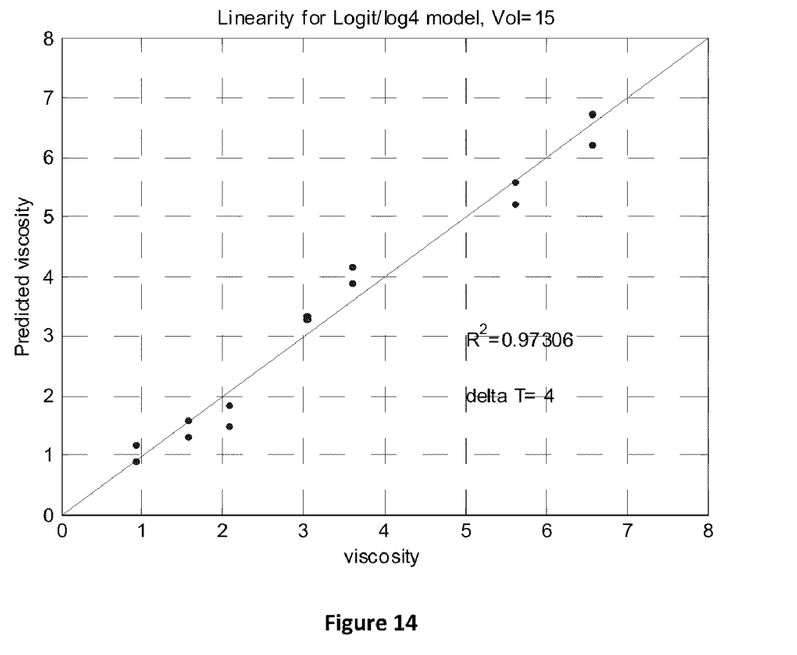
Figure 15:
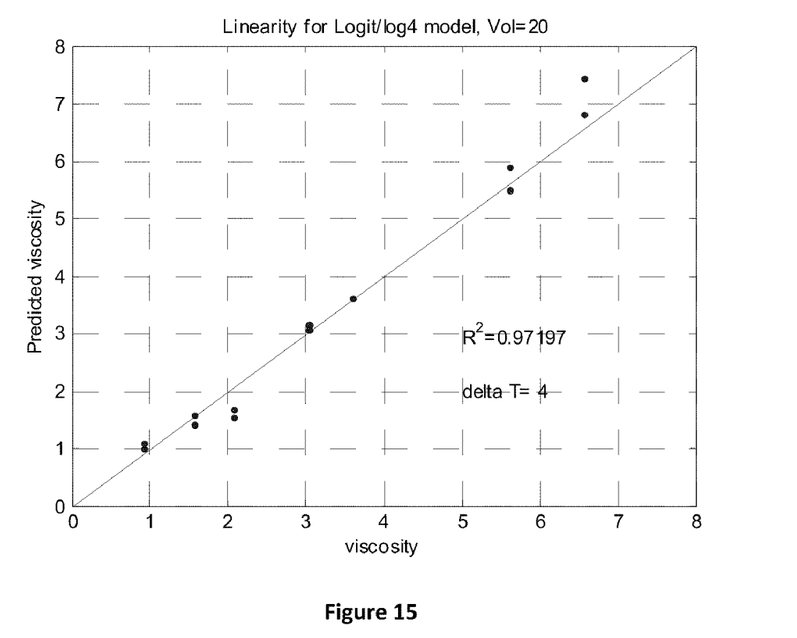

FIG. 8 shows viscosity measured directly from a viscometer plotted against the pressure rate.

FIGS. 9-15 show the linearity of a predicted viscosity determined by the method of the invention using the Log it/log 4 model vs. viscosity as determined by a viscometer for different volumes of liquid up to 20 μL.

As the figures show, the correlation between the viscosity measurement and viscosity calculation of the present invention is very high as shown by the correlation coefficients R2.

Thus by measuring three different pressures the rate of pressure rise R can be calculated which along with a curve fitting model such as log it/log 4 or simply manually using a calibration curve, the viscosity of the liquid being metered can be estimated.

In another embodiment, the three pressure measurements can be used to also estimate viscosity. The initial air volume inside the tip is $V_0$ and the initial pressure is the ambient pressure and is $p_0$ (also referred to as $P_{ref}$ as describe above). When the tip enters liquid, the liquid may enter the tip due to capillary pressure and gravity. As a result, $V_0$ may change to $V_1$ and $p_0$ may change to $p_1$. However, the product $p_1 V_1^\gamma = p_0 V_0^\gamma$ remains a constant according to the ideal gas law. After the pump stops, the liquid flow rate Q into or out of the tip is the same as the air volume change rate inside the tip as described above. Therefore, as also as described above, the rate of air volume change inside the tip can be used to determine the liquid flow rate. A positive value is assigned to the flow rate when fluid flows out of the tip and a negative value is assigned to the flow rate when fluid flows into the tip. The liquid flow rate Q(t) is related with air volume change $\Delta V(t) = V(t) - V_1$ by $$Q(t) = \frac{d(\Delta V)}{dt}. \quad (1)$$

The air pressure inside the tip is p(t) and is a function of time. The pressure difference between tip inside and the ambient is $\Delta p(t) = p(t) - p_0$. The liquid flow rate, pressure difference and liquid viscosity μ is related by $$Q(t) \sim \frac{\Delta p(t)}{\mu} \text{ or} \quad (2)$$

$$Q(t) = \beta \frac{\Delta p(t)}{\mu},$$

where the constant β is a positive number due to geometry effects to the flow.

From equations (1) and (2), the following relationship can be obtained, $$Q(t) = \frac{dV(t)}{dt} = \beta \frac{\Delta p(t)}{\mu}. \quad (3)$$

In a typical metering system, the pressure and air volume change is relatively small. The adiabatic ideal gas law is used to relate the air volume and pressure by $pV^\gamma = p_0 V_0^\gamma$. The volume change is related with pressure change by $$\Delta V = -\frac{V}{\gamma p}\Delta p = -\frac{V_0}{\gamma p}\left(\frac{p_0}{p}\right)^{\frac{1}{\gamma}}\Delta p \approx -\frac{V_0}{\gamma p_0}\Delta p. \quad (4)$$

Therefore $$\frac{V_0}{\gamma p_0}\frac{dp(t)}{dt} = -\beta\frac{p(t)-p_0}{\mu}. \quad (5)$$

The above equation (5) can be rearranged to obtain $$\frac{dp(t)}{p(t)-p_0} = \frac{\gamma p_0 \beta}{V_0}\frac{dt}{\mu}. \quad (6)$$

By integrating the above equation (6), the result is $$\ln[p(t)-p_0] = \frac{\gamma p_0 \beta}{V_0}\frac{t}{\mu} - C. \quad (7)$$

The air pressure as function of time can be written in the form of $$p(t) = Ae^{-\frac{\beta \gamma p_0}{V_0 \mu}} + B. \quad (8)$$

As t→∞, the pressure approaches the ambient and fluid flow stops. Therefore B=$p_0$=0. Therefore the pressure inside the system is related with viscosity as a function of time by $$p(t) = Ae^{-\frac{\beta \gamma p_0}{V_0 \mu}} = Ae^{\frac{k}{\mu}t}. \quad (9)$$

Where $k = \frac{\beta \gamma p_0}{V_0}$.

Let $\bar{p}(t)=p(t)-p_0$. Taking derivative of the above equation, the results is:

$$\dot{\bar{p}} = \frac{d\bar{p}}{dt} = \frac{k}{\mu}\bar{p}. \quad (10)$$

The viscosity $\mu$ is related with the ratio between relative pressure $\bar{p}$ and pressure rate $\dot{\bar{p}}$ by $$\mu = k\frac{\bar{p}}{\dot{\bar{p}}} \quad (11)$$

The above equation can be written in the form $$\frac{1}{\mu} = K\frac{\dot{\bar{p}}}{\bar{p}}. \quad (12)$$

The constants K and k are related with geometry, initial air pressure and volume inside the tip. The two constants are related by K=1/k. These constants can be determined by constructing a calibration curve using fluids having known viscosities and determining relative pressure difference ($\bar{p}$) and the rate of pressure change ($\dot{\bar{p}}$) from the three pressure measurements described above.

If the time at which the pump stops is set as t=0, the pressure inside the tip is the pressure when piston stops, $p_s$. Under these conditions the constant A in equation (9) is the air pressure inside the tip at the pump stop and A=$p_s$. Again, the viscosity can be estimated by three pressure measurements, $P_{ref}$, $P_{stop}$, $P_{stop'}$.

The viscosity can be obtained by using equation (11) or (12) with a linear function as the calibration curve. For equation (12), the reciprocal of viscosity (1/$\mu$) is calculated from the linear curve, and then the viscosity ($\mu$) is calculated with the reciprocal.

From the description above, it becomes apparent that the advantages of the present invention include:

1. Estimating viscosity with a small volume liquid aspiration or dispense by measuring only three pressure points in pressure signature during aspiration or dispense.
2. The algorithm used in the present invention is relatively simple to implement, particularly since pressure is the only property measured.
3. The invention helps in setting error detection thresholds to reduce false detection rates, particularly in diagnostic assays. For example, if an estimated viscosity is high, then the threshold for a clogged tipped notification may be set higher, because at a lower threshold the pressure change would likely be due to the higher viscosity liquid as opposed to a clogged tip. Likewise, if the estimated viscosity is low, then the threshold for clogged tip notification may be set lower.
4. Improved outcomes for the process the metering event is being used in. In one case improved precision and accuracy in the amount of fluid that is metered is realized based on knowing, by the estimation of the present method, fluid viscosity. For example, in the case of a high viscosity liquid, the metering pump for a metering probe can be set to over aspirate in order to aspirate the correct amount of liquid. Alternatively, the estimated viscosity can be used to alert an operator that the results of the process, such as a diagnostic assay, may be incorrect of view of the viscosity of the liquid which is outside of the normal range.

The viscosity estimation method of the present invention can be carried out on conventional metering equipment, such as those systems described in U.S. Pat. Nos. 6,484,556; 6,060,320; 5,750,881; and 5,540,081 all incorporated by reference in their entireties. The only requirement is the ability to measure pressure in the space between the liquid being aspirated and the pumping mechanism for the metering equipment. This is generally accomplished using a pressure transducer located between the tip of an aspirating/dispense probe and the pump.

In a method according to a preferred embodiment, the pressure inside the metering tip of the aspirating or dispensing probe is measured. This provides the reference pressure ($P_{ref}$) or ($\bar{p}$), one of the three pressure measurements of the present invention. The pumping mechanism is then actuated for a preselected amount of time or distance in either an aspirate or dispense mode. After the preselected amount of time or distance, the pump is stopped. At or about the time the moment the pump is stopped (t), the pressure transducer once again measures the pressure of the air between the liquid and the pump ($P_{stop}$). It should be noted that in many instances, the pressure is measured continuously or at discrete times intervals (time indexes) throughout the metering process. See, e.g., the pressure profile in FIG. 1. In such instances, the pressure $P_{stop}$ will be measured along with the other pressure measurements. The pressure at pump stop is the second of the pressure measurements used to estimate the viscosity according to the present invention.

After a set amount of time the pressure is measured once again. This pressure measurement is the third of the three pressure measurements used to estimate viscosity according the present invention. The time the third pressure measurement is taken can be any time (t') after pump stop and before the liquid flow into or out of the tip has equilibrated ($P_{stop'}$). In a preferred embodiment the pressure is measured a set number of time indexes after pump stop. Preferably, the pressure is measured 3 time indexes after pump stop ($P_{stop+3}$). A time index is the time between automated pressure measurements by the pressure transducer during a metering event. In one embodiment, a single time index is 5 milliseconds. These are the only measurements required to estimate viscosity according to the present invention.

A computer algorithm in a computer associated with the metering device can then be used to estimate the viscosity of the liquid based on the three pressure measurements. Using the first embodiment described above, the rate of pressure rise R is determined from the three pressure measurements $$R = \frac{P_{stop+3} - P_{stop}}{P_{stop} - P_{ref}}.$$

A calibration curve previously prepared for the fluid being measured can then be used with a calibration model such as log it/log 4 and R to calculate an estimated viscosity using the equation $$\mu = e^{\left\{-\frac{1}{\beta_3}\left[\beta_2 + \ln\left(\frac{\beta_1}{R-\beta_0}-1\right)\right]\right\}}$$

described above, or a linear calibration model can be used to estimate viscosity using an equation $$\mu = B0 + \frac{B1}{R+B2}$$

described above.

Using the second embodiment described above, the relative pressure $\bar{p}$ is calculated based on the difference between $P_{stop}$ and $P_{ref}$. The rate of pressure change $\dot{\bar{p}}$ at pump stop is calculated by $\dot{\bar{p}}=(P_{stop'}-P_{stop})/(t'-t)$. The viscosity is then estimated using the relative pressure, rate of pressure change and a calibration curve previously prepared for the fluid being measured by the relationship $$\mu = K\frac{\bar{p}}{\dot{\bar{p}}}.$$

Alternatively, a user can manually use a calibration curve manually graphed on paper of rate of pressure change or rise vs. known viscosity to arrive at an estimated viscosity using the calculated rate of pressure change or rise from the measured pressures for the particular liquid being estimated.

In a preferred embodiment, the viscosity estimation method according to the present invention can be used when a liquid is aspirated by a metering probe, such as a probe on a diagnostic analyzer. The method includes providing an aspirating probe. The probe has a probe tip and a pump, which are in fluid communication, generally through tubing. A pressure transducer is located such that it can measure the pressure of the gas, generally air, that is above the probe tip during the aspirate process. The pressure transducer in generally located between the probe tip and the pump mechanism.

The initial gas pressure in the tip of the aspirating probe prior to the liquid entering the liquid to be aspirated is measured. This can be done either before the probe tip enters the liquid or after the probe tip enters the liquid but before the pump is actuated.

The probe tip is moved into the liquid generally by means of a probe transport mechanism, e.g., a rack and pinion mechanism or hydraulic actuator. This results in a volume of gas being located between the top of the liquid and the pumping mechanism such as the piston of the piston pump. The pump is actuated in an amount to correspond to a selected volume of liquid. For example, the piston of a piston pump is moved a predetermined distance which corresponds to a selected volume of liquid to be aspirated.

The gas pressure in the volume of gas is measured when the pump stops and a short time thereafter to provide a pressure measurement at pump stop and pump stop plus a predetermined time. The pressure measurements are then used to estimate viscosity according to the present invention. In a preferred embodiment, the liquid is a sample of bodily fluid, such as whole blood, plasma, serum, urine or saliva. In another embodiment, the liquid is one or more of a reagent, wash fluid, calibrator fluid or control fluid, such as those used in diagnostic analyzers. The estimated viscosity can then be used elsewhere in the process.

As discussed above one application of the viscosity estimation technique of the present invention is in a diagnostic analyzer for analyzing the amount of analyte in a sample, such as a biological sample. Automated diagnostic analyzers are a fixture in the clinical laboratory. The range of analyzers and methodologies in use is large. Some examples include spectrophotometric absorbance assay such as end-point reaction analysis and rate of reaction analysis, turbidimetric assays, nephelometric assays, radiative energy attenuation assays (such as those described in U.S. Pat. Nos. 4,496,293 and 4,743,561), ion capture assays, colorimetric assays, fluorometric assays, electrochemical detection systems, potentiometric detection systems, and immunoassays. Some or all of these techniques can be done with classic wet chemistries which utilize a cuvette; ion-specific electrode analysis (ISE); thin film formatted "dry" slide chemistries; bead and tube formats or microtiter plates; and the use of magnetic particles. U.S. Pat. No. 5,885,530 provides a description useful for understanding the operation of a typical automated analyzer for conducting immunoassays in a bead and tube format and is incorporated herein by reference. Other typical diagnostic analyzers include those described in U.S. Pat. Nos. 7,402,282, 7,312,084, and 7,250,303 all incorporated herein by reference in their entireties.

In an operation of a typical diagnostic analyzer, sample is aspirated as described above. The sample is then dispensed in a sample holder. The sample holder can include those known in the art as described above. Dry slides, cuvettes and streptavidin coated wells are particularly preferred. A particularly preferred application of the present invention is to aspirate a sample liquid from a larger metering tip that has been previously sealed at the bottom, while sample is present in the tip. These type of sealed tips are called a Cuvetip™ sold by Ortho-Clinical Diagnostics, Inc. and are described for example in U.S. Pat. No. 6,797,518 and in U.S. Published Patent Application No. 2003-0022380 A1 published Jan. 30, 2003, both of which are incorporated by reference in their entireties. Depending on the system being utilized various reagents may be added. The sample with reagents may be incubated for a selected amount of time, and then a measurement taken. For example, in chemistry analyzers the analysis can be a colorimetric analysis that utilizes a photometer operating at a specific wavelength. In immunoassays, the analysis can be made by chemiluminesence with the emitted light being measured by a luminometer or by fluorescence. Such measurement systems, per se, are well known in the art. As described above, the viscosity estimation according to the present invention can be used to compensate the diagnostic instrument for viscosity to improve accuracy and precision, such as by adjusting the displacement of the pump; or the viscosity estimation can be used to notify an operator or otherwise signal an alert that a viscosity measurement is outside of a predetermined value or range and any result should be considered accordingly.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A method for estimating the viscosity of a liquid in an aspirating or dispensing probe, comprising:

measuring a reference pressure which is the pressure inside a metering tip when no dispense or aspirate is occurring ($P_{ref}$);

dispensing or aspirating a liquid having a volume of air between the liquid and the pumping mechanism of the probe;

stopping the aspirate or dispense;

measuring the pressure ($P_{stop}$) inside the tip at a time (t) which is the time when the aspirate or dispense is stopped;

measuring the pressure ($P_{stop'}$) inside the tip at a time (t') after t;

calculating a relative pressure difference ($\bar{p}$) which is the difference between $P_{stop}$ and $P_{ref}$;

calculating the rate of pressure change ($\dot{\bar{p}}$) at $P_{stop}$ by $\dot{\bar{p}}=(P_{stop'}-P_{stop})/(t'-t)$; and estimating viscosity as a function of $\bar{p}$ and $\dot{\bar{p}}$.

2. The method according to claim 1, wherein $P_{ref}$ is ambient pressure or $P_{ref}$ is the pressure when the tip is in the fluid and is effected by gravity and capillary forces.

3. The method according to claim 2, wherein $P_{ref}$ is substantially the same when $P_{ref}$ is determined by ambient pressure or pressure when the fluid is inside the tip.

4. The method according to claim 1, wherein the estimating further comprises using the equation:

$$\mu = K\frac{\bar{p}}{\dot{\bar{p}}}$$

wherein µ is viscosity.

5. The method as claimed in claim 4, wherein K is predetermined by a calibration curve generated using different viscosities for the fluid being aspirated or dispensed.

6. The method as claim in claim 1, further comprising:
calculating a rate of pressure rise $$(R) = \frac{P_{stop+3} - P_{stop}}{P_{stop} - P_{ref}};$$

and
estimating viscosity as a function of R, wherein $P_{stop+3}$ is the pressure measured 3 time indexes after the aspirate or dispense is stopped.

7. The method as claimed in claim 6, wherein viscosity is estimated as a function of R using a non-linear calibration curve.

8. The method as claimed in 7, wherein the viscosity is estimated by:

$$\mu = e^{\left\{-\frac{1}{\beta_3}\left[\beta_2 + ln\left(\frac{\beta_1}{R-\beta_0}-1\right)\right]\right\}}$$

wherein $\beta_0$, $\beta_1$, $\beta_2$, and $\beta_3$ are constants determined by a non-linear calibration curve.

9. The method as claimed in claim 6, wherein viscosity is estimated as a function of R using a linear calibration curve.

10. The method as claimed in claim 6, wherein the viscosity is estimated by $$\mu = B0 + \frac{B1}{R+B2},$$

wherein B0, B1 and B2 are determined by a linear calibration curve.

11. The method as claimed in claim 1, wherein t' is measured 15 milliseconds after t.

12. The method as claimed in claim 1, wherein the amount of liquid being aspirated or dispensed is $\leq 10$ µL.

13. The method as claimed in claim 1, wherein the amount of liquid being aspirated or dispensed is $\leq 5$ µL.

14. The method as claimed in claim 1, wherein the amount of liquid being aspirated or dispensed is $\leq 2$ µL.

15. The method as claimed in claim 1, wherein the liquid is a sample of bodily fluid.

16. The method as claimed in claim 15, wherein the bodily fluid is one or more of whole blood, plasma, serum, urine or saliva.

17. The method as claimed in claim 1, wherein the liquid is one or more of a reagent, wash fluid, calibrator fluid or control fluid.

18. A method for aspirating a selected amount of liquid comprising:

providing an aspirating probe which comprises a probe tip and a pump, wherein the probe tip and pump are in fluid communication;

measuring a reference pressure which is the pressure inside a metering tip when no dispense or aspirate is occurring ($P_{ref}$);

moving the tip into the liquid, whereby a volume of gas is located between the top of the liquid and the pump, wherein the reference pressure is measured before or after the tip enters the liquid;

actuating the pump for a duration or distance which corresponds to a selected volume of liquid to be aspirated;

stopping the aspirate or dispense;

measuring the pressure ($P_{stop}$) inside the tip at a time (t) which is the time when the aspirate or dispense is stopped;

measuring the pressure ($P_{stop'}$) inside the tip at a time (t') after t;

calculating a relative pressure difference ($\bar{p}$) which is the difference between $P_{stop}$ and $P_{ref}$;

calculating the rate of pressure change ($\dot{\bar{p}}$) at $P_{stop}$ by $\dot{\bar{p}}=(P_{stop'}-P_{stop})/(t'-t)$;

estimating viscosity as a function of $\bar{p}$ and $\dot{\bar{p}}$; and compensating for viscosity by either notifying an operator if the estimated viscosity is outside a predetermined range, or adjusting the actuation of the pump based on the estimated viscosity.

19. The method for aspirating a selected amount of liquid as claimed in claim 18, wherein the pump is a piston pump and wherein the piston of the piston pump is moved a predetermined distance which corresponds to a selected volume of liquid to be aspirated.

20. A method of analyzing a sample for an analyte, comprising:

providing a source of a sample;

providing an aspirating probe which comprises a probe tip and a pump, wherein the probe tip and pump are in fluid communication;

measuring a reference pressure which is the pressure inside a metering tip when no dispense or aspirate is occurring ($P_{ref}$);

moving the tip into the liquid, whereby a volume of gas is located between the top of the liquid and the pump, wherein the reference pressure is measured before or after the tip enters the liquid;

actuating the pump for a duration or distance which corresponds to a selected volume of liquid to be aspirated;

stopping the aspirate or dispense;

measuring the pressure ($P_{stop}$) inside the tip at a time (t) which is the time when the aspirate or dispense is stopped;

measuring the pressure ($P_{stop'}$) inside the tip at a time (t') after t;

calculating a relative pressure difference ($\bar{p}$) which is the difference between $P_{stop}$ and $P_{ref}$;

calculating the rate of pressure change ($\bar{\dot{p}}$) at $P_{stop}$ by $\bar{\dot{p}} = (P_{stop'} - P_{stop})/(t'-t)$; and estimating viscosity as a function of $\bar{p}$ and $\bar{\dot{p}}$; and compensating for viscosity by either notifying an operator if the estimated viscosity is outside a pre-determined range, or adjusting the actuation of the pump based on the estimated viscosity.

* * * * *